US011833455B2

(12) United States Patent
Kamba et al.

(10) Patent No.: US 11,833,455 B2
(45) Date of Patent: Dec. 5, 2023

(54) SEPARATION RECOVERY SYSTEM AND SEPARATION RECOVERY METHOD

(71) Applicant: Murata Manufacturing Co., Ltd., Nagaokakyo (JP)

(72) Inventors: Seiji Kamba, Nagaokakyo (JP); Takashi Kondo, Nagaokakyo (JP); Masaru Banju, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 0 days.

(21) Appl. No.: 18/065,418

(22) Filed: Dec. 13, 2022

(65) Prior Publication Data
US 2023/0116829 A1 Apr. 13, 2023

Related U.S. Application Data

(60) Division of application No. 16/895,357, filed on Jun. 8, 2020, now abandoned, which is a continuation of
(Continued)

(30) Foreign Application Priority Data

Dec. 28, 2017 (JP) ................. 2017-253052

(51) Int. Cl.
B01D 29/68 (2006.01)
B01D 29/01 (2006.01)
(Continued)

(52) U.S. Cl.
CPC ............. B01D 29/68 (2013.01); B01D 29/01 (2013.01); B01D 29/663 (2013.01); B01D 29/90 (2013.01);
(Continued)

(58) Field of Classification Search
CPC ........ B01D 26/68; B01D 37/00; B01D 35/00; B01D 29/68; B01D 29/0004;
(Continued)

(56) References Cited

U.S. PATENT DOCUMENTS 9,631,179 B2 * 4/2017 Hvichia ............ B01L 3/502753
2007/0025882 A1 * 2/2007 Zuppiger ................ B01L 3/021
422/400
(Continued)

FOREIGN PATENT DOCUMENTS

CN 106795476 A 5/2017
JP 2006007179 A 1/2006
(Continued)

OTHER PUBLICATIONS

International Search Report Issued for PCT/JP2018/045863, dated Mar. 19, 2019.
(Continued)

Primary Examiner — Allison G Fitzsimmons
(74) Attorney, Agent, or Firm — ArentFox Schiff LLP

(57) ABSTRACT

A separation recovery system for separating and recovering an object to be separated includes a metal porous membrane which has a first principal surface and a second principal surface facing the first principal surface and has a plurality of through-holes extending between the first principal surface and the second principal surface, a supply device which supplies a first fluid containing the object to be separated from the first principal surface of the metal porous membrane toward the second principal surface, and a backwash device which supplies a second fluid containing a plurality of particles larger than a size of the plurality of through-holes of the metal porous membrane in a direction from the second principal surface of the metal porous membrane toward the first principal surface.

10 Claims, 12 Drawing Sheets

Related U.S. Application Data application No. PCT/JP2018/045863, filed on Dec. 13, 2018.

(51) Int. Cl.
*B01D 29/66* (2006.01)
*B01D 29/90* (2006.01)
*B01D 71/02* (2006.01)

(52) U.S. Cl.
CPC ........ *B01D 71/022* (2013.01); *B01D 2221/10* (2013.01); *B01D 2257/91* (2013.01); *B01D 2321/04* (2013.01); *B01D 2325/021* (2013.01)

(58) Field of Classification Search
CPC .... B01D 29/663; B01D 29/90; B01D 71/022; B01D 2221/10; B01D 2257/91; B01D 2321/00; B01D 2321/04; B01D 2321/12; B01D 2321/14; B01D 2321/16; B01D 2321/24; B01D 2321/30; B01D 2325/021; B01D 41/00; B01D 41/04; B01D 61/00; B01D 61/02; B01D 61/14; B01D 61/12; B01D 61/22; B01D 63/08; B01D 63/10; B01D 65/02; B01D 65/08; B01D 2315/20; C02F 3/00
See application file for complete search history.

(56) References Cited

U.S. PATENT DOCUMENTS

| | | |
|---|---|---|
| 2009/0148946 A1 | 6/2009 | Haga et al. |
| 2011/0233148 A1 | 9/2011 | Antonchuk et al. |
| 2018/0362917 A1 | 12/2018 | Kondo et al. |

FOREIGN PATENT DOCUMENTS

| | | |
|---|---|---|
| JP | 2009136246 A | 6/2009 |
| WO | 2010130303 A1 | 11/2010 |
| WO | 2012057495 A2 | 5/2012 |
| WO | 2017159367 A1 | 9/2017 |

OTHER PUBLICATIONS

Written Opinion of the International Searching Authority issued for PCT/JP2018/045863, dated Mar. 19, 2019.

* cited by examiner

SEPARATION RECOVERY SYSTEM AND SEPARATION RECOVERY METHOD

CROSS REFERENCE TO RELATED APPLICATIONS

The present application is a divisional of application Ser. No. 16/895,357, filed Jun. 8, 2020, which is a continuation of International application No. PCT/JP2018/045863, filed Dec. 13, 2018, which claims priority to Japanese Patent Application No. 2017-253052, filed Dec. 28, 2017, the entire contents of each of which are incorporated herein by reference.

FIELD OF THE INVENTION

The present invention relates to a separation recovery system and a separation recovery method.

BACKGROUND OF THE INVENTION

Patent Document 1 discloses a recovery method including capturing cells in a liquid using a membrane filter and recovering the cells captured on the membrane filter by performing backwashing.

Patent Document 1: Japanese Unexamined Patent Application Publication No. 2009-136246

SUMMARY OF THE INVENTION

However, in the recovery method of Patent Document 1, there is yet room for improvement from the viewpoint of improving the recovery ratio of the object to be separated.

An object of the present invention is to provide a separation recovery system and a separation recovery method capable of improving the recovery ratio of an object to be separated.

In an aspect of the present invention, a separation recovery system for separating and recovering an object to be separated includes a metal porous membrane which has a first principal surface and a second principal surface facing the first principal surface and has a plurality of through-holes extending between the first principal surface and the second principal surface, a supply device which supplies a first fluid containing the object to be separated from the first principal surface of the metal porous membrane toward the second principal surface, and a backwash device which supplies a second fluid containing a plurality of particles larger than a size of the plurality of through-holes of the metal porous membrane in a direction from the second principal surface of the metal porous membrane toward the first principal surface.

In an aspect of the present invention, a separation recovery method for separating and recovering an object to be separated includes supplying a first fluid containing the object to be separated from a first principal surface of a metal porous membrane having a plurality of through-holes toward a second principal surface facing the first principal surface so that the object to be separated is captured on the first principal surface of the metal porous membrane; supplying a second fluid containing a plurality of particles larger than a size of the plurality of through-holes of the metal porous membrane to the metal porous membrane on which the object to be separated has been captured in a direction from the second principal surface of the metal porous membrane toward the first principal surface; and capturing the plurality of particles on the second principal surface of the metal porous membrane.

According to the present invention, it is possible to provide a separation recovery system and a separation recovery method capable of improving the recovery ratio of an object to be separated.

DETAILED DESCRIPTION OF THE PREFERRED EMBODIMENTS

Figure 1:
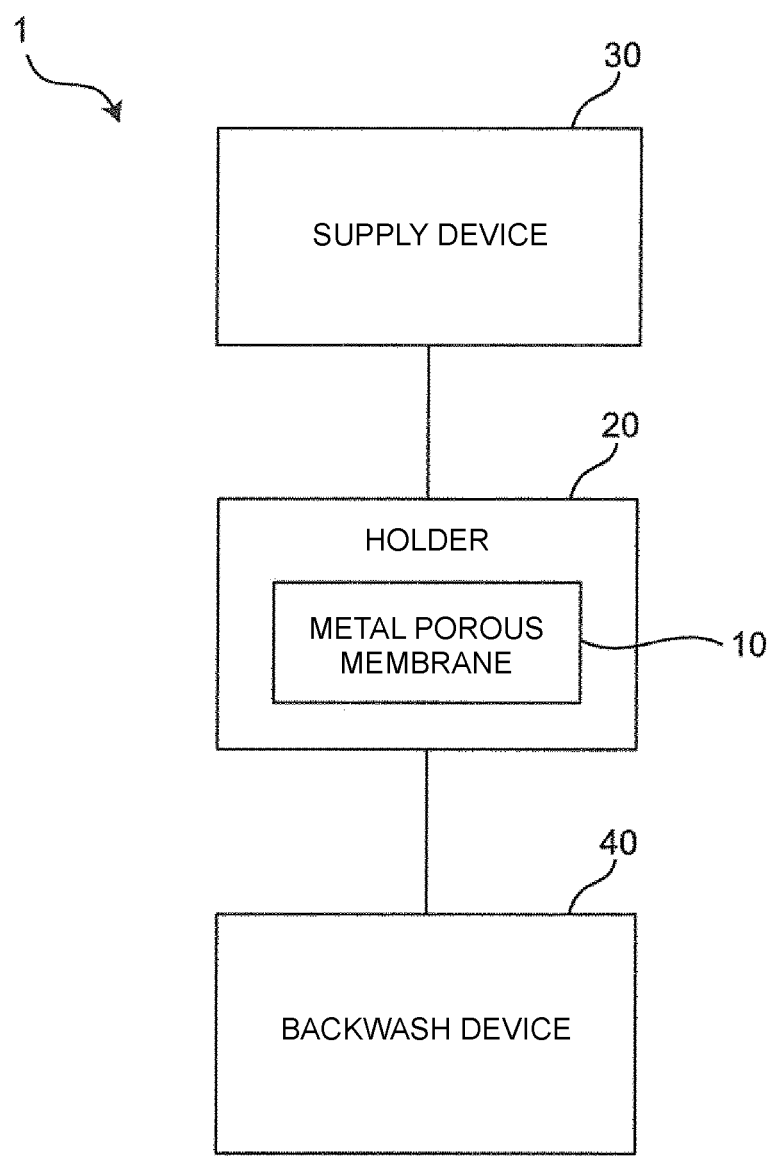
FIG. 1 is a schematic block diagram of an example of a separation recovery system according to Embodiment 1 of the present invention.

As a method for separating and recovering an object to be separated in a fluid, there is known a separation recovery method using a membrane filter. In the separation recovery method using a membrane filter, an object to be separated in a fluid is captured by the membrane filter, and by performing backwashing, the object to be separated is recovered.

A membrane filter has a structure in which a plurality of through-holes are formed in different directions three-dimensionally. That is, in the membrane filter, the plurality of through-holes are not formed regularly, straight in the thickness direction of the filter. Therefore, in the membrane filter, a fluid has difficulty in passing through the through-holes, and the pressure drop during passing of the fluid increases.

In such a membrane filter, in order to separate an object to be separated from a fluid, for example, by pressing the fluid against the membrane filter, the fluid is passed through the membrane filter. In the case where the fluid is passed through the membrane filter by pressing, it is necessary to increase the pressing force in response to the pressure drop. In the case where the object to be separated is an object, such as cells or bacteria, that is susceptible to deformation, when the pressing force is increased, the object to be separated may be deformed and pass through the through-holes or may become stuck in the through-holes, resulting in difficulty in recovery of the object to be separated by backwashing in some cases.

As described above, in a method for separating and recovering an object to be separated using a membrane filter, it is difficult to improve the recovery ratio. Accordingly, the present inventors have found that an object to be separated in a fluid is separated and recovered using a metal porous membrane.

In a metal porous membrane, a plurality of through-holes are formed in the same direction three-dimensionally, i.e., formed regularly, straight in the thickness direction of the membrane. Furthermore, the thickness of the metal porous membrane is smaller than the thickness of the membrane filter. Therefore, the metal porous membrane is advantageous in that the pressure drop during passing of the fluid can be decreased, and the pressing force can be decreased, compared with the membrane filter. The metal porous membrane is also advantageous in that the object to be separated can be easily recovered by backwashing, compared with the membrane filter.

However, even in the separation recovery method using a metal porous membrane, there is yet room for improvement from the viewpoint of improving the recovery ratio.

In a metal porous membrane, in the case where an object to be separated is recovered by backwashing, when the object to be separated is removed from through-holes as the backwashing proceeds, a fluid for backwashing is allowed to flow through the through-holes from which the object to be separated has been removed, and consequently, the force that detaches the object to be separated remaining on the metal porous membrane is decreased. Therefore, as the backwashing proceeds, it becomes difficult to detach the object to be separated from the metal porous membrane, resulting in difficulty in recovery of the object to be separated. This is a problem newly found by the present inventors.

In order to solve this problem, the present inventors have found that by performing backwashing, using a fluid containing a plurality of particles larger than through-hole of the metal porous membrane, the recovery ratio can be improved, and thus the present invention has been accomplished.

In an aspect of the present invention, a separation recovery system for separating and recovering an object to be separated includes a metal porous membrane which has a first principal surface and a second principal surface facing the first principal surface and has a plurality of through-holes extending between the first principal surface and the second principal surface, a supply device which supplies a first fluid containing the object to be separated from the first principal surface of the metal porous membrane toward the second principal surface, and a backwash device which supplies a second fluid containing a plurality of particles larger than a size of the plurality of through-holes of the metal porous membrane in a direction from the second principal surface of the metal porous membrane toward the first principal surface.

In such a configuration, the recovery ratio of the object to be separated can be improved.

In the separation recovery system, the backwash device may supply the second fluid containing the plurality of particles in the direction from the second principal surface of the metal porous membrane toward the first principal surface when a pressure on the second principal surface side of the metal porous membrane is higher than a pressure on the first principal surface side.

In such a configuration, detachment of the object to be separated from the metal porous membrane is caused by a difference in pressure between the second principal surface side and the first principal surface side of the metal porous membrane, and the object to be separated can be easily recovered. Thus, the recovery ratio can be further improved.

In the separation recovery system, the plurality of particles may be smaller than a hole pitch of the plurality of through-holes of the metal porous membrane.

In such a configuration, the particles become easily captured in the through-holes. Thus, the object to be separated can be easily detached from the metal porous membrane, and the recovery ratio of the object to be separated can be further improved.

In the separation recovery system, the number of the plurality of particles may be greater than the number of the plurality of through-holes of the metal porous membrane.

In such a configuration, the particles become easily captured in the through-holes. Thus, the object to be separated can be easily detached from the metal porous membrane, and the recovery ratio of the object to be separated can be further improved.

In the separation recovery system, the shape of each of the plurality of particles may be spherical.

In such a configuration, the object to be separated can be easily detached from the metal porous membrane, and the recovery ratio of the object to be separated can be further improved.

In the separation recovery system, the shape of each of the plurality of through-holes of the metal porous membrane may be circular when viewed from the thickness direction of the metal porous membrane.

In such a configuration, the object to be separated can be more easily detached from the metal porous membrane, and the recovery ratio of the object to be separated can be further improved.

The cross-sectional shape of each of the plurality of particles may be different from the shape of the through-hole of the metal porous membrane.

In such a configuration, while decreasing the pressure applied on the metal porous membrane, the object to be separated can be easily detached from the metal porous membrane, and the recovery ratio of the object to be separated can be further improved.

In an aspect of the present invention, a separation recovery method for separating and recovering an object to be separated includes supplying a first fluid containing the object to be separated from a first principal surface of a metal porous membrane having a plurality of through-holes toward a second principal surface facing the first principal surface so that the object to be separated is captured on the first principal surface of the metal porous membrane; supplying a second fluid containing a plurality of particles larger than a size of the plurality of through-holes of the metal porous membrane to the metal porous membrane on which the object to be separated has been captured in a direction from the second principal surface of the metal porous membrane toward the first principal surface; and capturing the plurality of particles on the second principal surface of the metal porous membrane.

In such a configuration, the recovery ratio of the object to be separated can be improved.

In the separation recovery method, a pressure on a second principal surface side of the metal porous membrane is preferably set higher than a pressure on a first principal surface side of the metal porous membrane when supplying the second fluid containing the plurality of particles in the direction from the second principal surface of the metal porous membrane toward the first principal surface of the metal porous membrane.

In such a configuration, detachment of the object to be separated from the metal porous membrane is caused by a difference in pressure between the second principal surface side and the first principal surface side of the metal porous membrane, and the object to be separated can be easily recovered. Thus, the recovery ratio can be further improved.

In the separation recovery method, the plurality of particles may be smaller than a hole pitch of the plurality of through-holes of the metal porous membrane.

In such a configuration, the particles become easily captured in the through-holes. Thus, the object to be separated can be easily detached from the metal porous membrane, and the recovery ratio of the object to be separated can be further improved.

In the separation recovery method, the number of the plurality of particles may be greater than the number of the plurality of through-holes of the metal porous membrane.

In such a configuration, the particles become easily captured in the through-holes. Thus, the object to be separated can be easily detached from the metal porous membrane, and the recovery ratio of the object to be separated can be further improved.

In the separation recovery method, the shape of each of the plurality of particles may be spherical.

In such a configuration, the object to be separated can be more easily detached from the metal porous membrane, and the recovery ratio of the object to be separated can be further improved.

In the separation recovery method, the shape of each of the plurality of through-holes of the metal porous membrane may be circular when viewed from the thickness direction of the metal porous membrane.

In such a configuration, the object to be separated can be more easily detached from the metal porous membrane, and the recovery ratio of the object to be separated can be further improved.

In the separation recovery method, the cross-sectional shape of each of the plurality of particles may be different from the shape of the through-hole of the metal porous membrane.

In such a configuration, while decreasing the pressure applied on the metal porous membrane, the object to be separated can be easily detached from the metal porous membrane, and the recovery ratio of the object to be separated can be further improved.

Embodiment 1 of the present invention will be described below with reference to the accompanying drawings. Furthermore, in the drawings, in order to facilitate explanation, the individual elements are indicated exaggeratedly.

Embodiment 1

[Separation Recovery System]

FIG. 1 is a schematic block diagram of an example of a separation recovery system 1 according to Embodiment 1 of the present invention. As shown in FIG. 1, the separation recovery system 1 includes a metal porous membrane 10, a holder 20, a supply device 30, and a backwash device 40. In Embodiment 1, the metal porous membrane 10 is held by the holder 20. Furthermore, the supply device 30 and the backwash device 40 are each detachably connected to the holder 20.

Embodiment 1 describes an example in which the separation recovery system 1 includes the holder 20. However, the present invention is not limited thereto. In the separation recovery system 1, the holder 20 is provided considering the convenience of the system, and is not an essential member.

In the present description, the term "object to be separated" means an object to be separated from a fluid. Examples of the object to be separated include a substance derived from an organism, such as a cell, a bacterium, and a virus. Examples of the cell include ova, spermatozoa, induced pluripotent stem cells (iPS cells), ES cells, stem cells, mesenchymal stem cells, mononuclear cells, single cells, cell masses, floating cells, adherent cells, nerve cells, white blood cells, lymphocytes, cells for regenerative medicine, self cells, cancer cells, circulating tumor cells (CTCs), HL-60, HELA, yeasts, and the like. Examples of the bacterium include Gram-positive bacteria, Gram-negative bacteria, colon bacilli, staphylococci, tubercle bacilli, and the like. Examples of the virus include DNA viruses, RNA viruses, rotaviruses, (bird) influenza viruses, yellow fever viruses, dengue fever viruses, encephalitis viruses, hemorrhagic fever viruses, immunodeficiency viruses, and the like. Note that the object to be separated may be an inorganic substance such as a ceramic particle, a binder particle, or an aerosol, an organic substance, or a metal.

In the present description, the term "fluid" means a liquid or a gas.

<Metal Porous Membrane>

Figure 2:
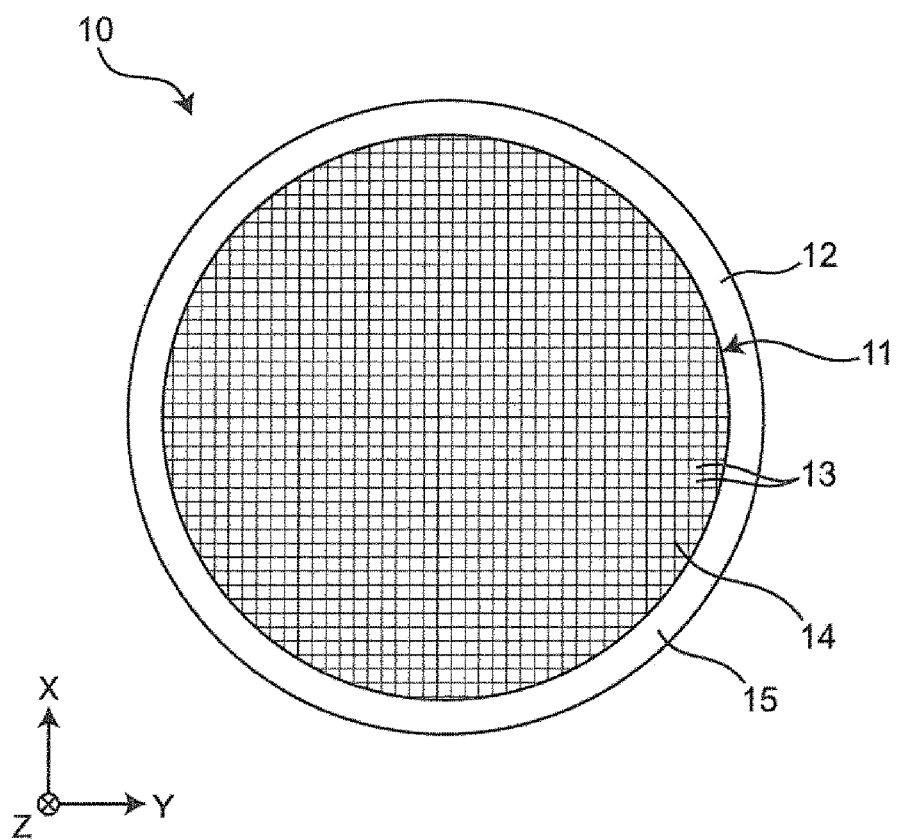
FIG. 2 is a schematic diagram of an example of a metal porous membrane in the separation recovery system according to Embodiment 1 of the present invention.

FIG. 2 is a schematic diagram of an example of the metal porous membrane 10 in the separation recovery system 1 according to Embodiment 1 of the present invention. The X, Y, and Z directions in FIG. 2 represent the longitudinal, transverse, and thickness directions of the metal porous membrane 10, respectively. As shown in FIG. 2, the metal porous membrane 10 includes a membrane portion 11 and a frame portion 12 provided on the outer circumference of the membrane portion 11.

The metal porous membrane 10 is a sheet-like structure which is held by the holder 20 at the frame portion 12 and captures the object to be separated in a fluid at the membrane portion 11. In Embodiment 1, the external shape of the metal porous membrane 10 is, for example, circular when viewed from the Z direction. Note that the external shape of the metal porous membrane 10 is not limited to circular, but may be square, rectangular, polygonal, elliptic, or the like.

Figure 3:
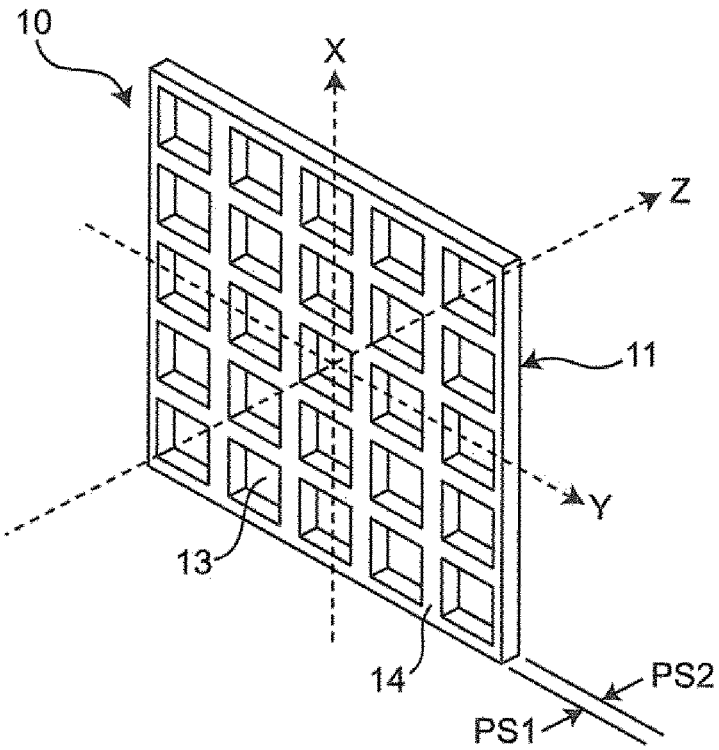
FIG. 3 is an enlarged perspective view showing a part of a membrane portion of the metal porous membrane shown in FIG. 2.
Figure 4:
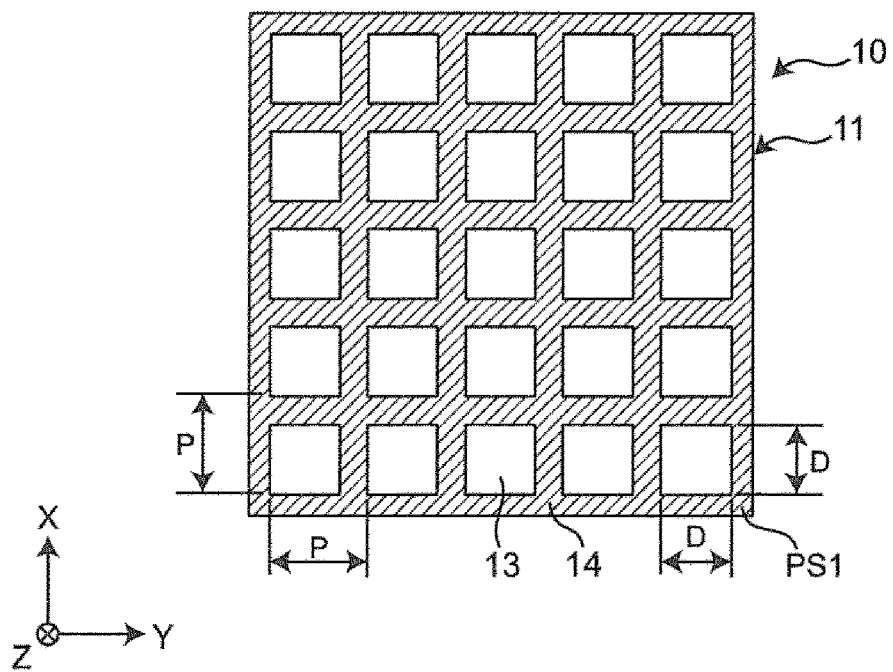
FIG. 4 is a schematic view of a part of the membrane portion of the metal porous membrane shown in FIG. 3, viewed from the thickness direction.

The membrane portion 11 is formed of a filter base portion 14 provided with a plurality of through-holes 13. FIG. 3 is an enlarged perspective view showing a part of the membrane portion 11 of the metal porous membrane 10 shown in FIG. 2. FIG. 4 is a schematic view of a part of the membrane portion 11 of the metal porous membrane 10 shown in FIG. 3. As shown in FIGS. 3 and 4, the membrane portion 11 has a first principal surface PS1 and a second principal surface PS2 which face each other. The plurality of through-holes 13 are formed so as to penetrate between the first principal surface PS1 and the second principal surface PS2 and are formed periodically. Specifically, the plurality of through-holes 13 are formed in a matrix at equal intervals in the membrane portion 11.

In Embodiment 1, as shown in FIG. 4, the through-holes 13 each have a square shape with a side D, when viewed from the first principal surface PS1 side of the membrane portion 11, i.e., from the Z direction. The side D of the through-hole 13 is appropriately designed depending on the size, form, properties, elasticity, or amount of the object to be separated. Furthermore, the hole pitch P of the through-holes 13 is also appropriately designed depending on the size, form, properties, elasticity, or amount of the object to be separated. Here, the hole pitch P of the square through-holes 13 means the distance between one side of any through-hole 13 and one side of its adjacent through-hole 13.

For example, the opening ratio of the membrane portion 11 is 5% or more, and preferably 4.5% or more. In such a configuration, the fluid passage resistance of the membrane portion 11 can be reduced. Note that the opening ratio can be calculated by (area occupied by the through-holes 13)/(projected area of the first principal surface PS1 in the membrane portion 11 on the assumption that the through-holes 13 are not opened).

The thickness of the membrane portion 11 is preferably more than 0.01 times and equal to or less than 10 times the size (the length of one side D) of the through-hole 13. More preferably, the thickness of the membrane portion 11 is more than 0.05 times and equal to or less than 7 times the size (the length of one side D) of the through-hole 13. In such a configuration, the resistance of the membrane portion 11 to a fluid can be reduced, and the treatment time can be shortened.

As shown in FIG. 4, in a through-hole 13, an opening on the first principal surface PS1 side and an opening on the second principal surface PS2 side communicate with each other through a continuous wall surface. Specifically, the through-hole 13 is formed such that the opening on the first principal surface PS1 side can be projected to the opening on the second principal surface PS2 side. That is, the through-hole 13 is provided such that the opening on the first principal surface PS1 side overlaps the opening on the second principal surface PS2 side when the membrane portion 11 is viewed from the first principal surface PS1 side. In Embodiment 1, the through-hole 13 is provided such that its inner wall is substantially perpendicular to each of the first principal surface PS1 and the second principal surface PS2.

In Embodiment 1, the shape of the through-hole 13 projected to a plane perpendicular to the first principal surface PS1 of the membrane portion 11 (cross-sectional shape) is rectangular. Specifically, the cross-sectional shape of the through-hole 13 is rectangular, with the length of one side in the radial direction of the membrane portion 11 being larger than the length of one side in the thickness direction of the membrane portion 11. Note that the cross-sectional shape of the through-hole 13 is not limited to rectangular, but may be, for example, parallelogrammatic, trapezoidal, or the like.

In Embodiment 1, the through-holes 13 are provided at equal intervals in two arrangement directions parallel to sides of the square when viewed from the first principal surface PS1 side of the membrane portion 11 (the Z direction), i.e., in the X and Y directions shown in FIG. 4. In such a manner, by providing the through-holes 13 in a square lattice arrangement, the opening ratio can be increased, and the fluid passage resistance (pressure drop) of the membrane portion 11 can be reduced.

Note that the arrangement of the through-holes 13 is not limited to the square lattice arrangement, but may be, for example, a quasi-periodic arrangement or periodic arrangement. As a tetragonal arrangement as an example of the periodic arrangement, a rectangular arrangement in which intervals in two arrangement directions are not equal may be used. Furthermore, a triangular lattice arrangement, equilateral triangular lattice arrangement, or the like may be used. Note that, as long as a plurality of through-holes 13 are formed in the membrane portion 11, the arrangement is not particularly limited.

A material constituting the filter base portion 14 which is a base portion of the membrane portion 11 contains, as a main component, a metal and/or a metal oxide. Examples of the material constituting the filter base portion 14 include gold, silver, copper, platinum, nickel, palladium, alloys thereof, and oxides thereof.

The frame portion 12 is provided on the outer circumference of the membrane portion 11 and is ring-shaped when viewed from the first principal surface PS1 side of the membrane portion 11. The frame portion 12 is a portion where the through-holes 13 are not provided in the metal porous membrane 10. The thickness of the frame portion 12 may be larger than the thickness of the membrane portion 11. In such a configuration, the mechanical strength of the metal porous membrane 10 can be enhanced.

<Holder>

The holder 20 is a member which holds the metal porous membrane 10 and is detachably mounted on the supply device 30 and the backwash device 40.

Figure 5A:
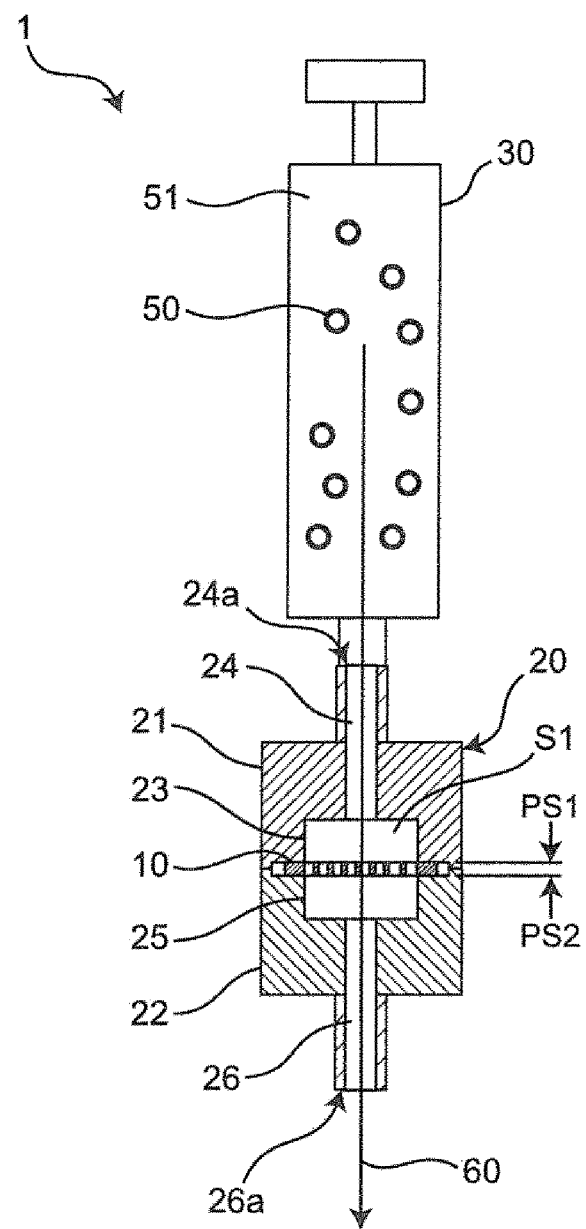
FIG. 5A is a schematic diagram of an example of a separation recovery system according to Embodiment 1 of the present invention.
Figure 5B:
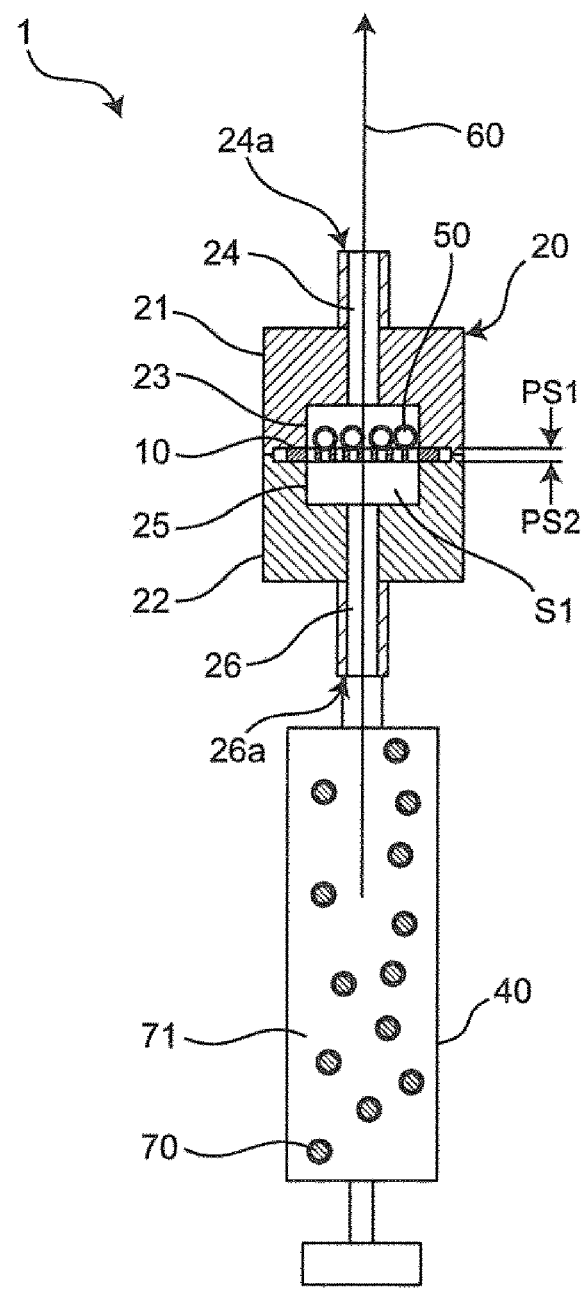
FIG. 5B is a schematic diagram of an example of a separation recovery system according to Embodiment 1 of the present invention.

FIGS. 5A and 5B are each a schematic diagram of an example of a separation recovery system according to Embodiment 1 of the present invention. FIG. 5A schematically shows a structure in which a supply device 30 is mounted on a holder 20. FIG. 5B schematically shows a structure in which a backwash device 40 is mounted on a holder 20.

As shown in FIGS. 5A and 5B, the holder 20 includes a first holding member 21 and a second holding member 22. The first holding member 21 and the second holding member 22 sandwich the frame portion 12 of the metal porous membrane 10 in the thickness direction of the metal porous membrane 10, thereby holding the metal porous membrane 10 inside the holder 20.

The first holding member 21 is formed in a substantially cylindrical shape and has, on the inside thereof, a first recessed portion 23 in which the metal porous membrane 10 is arranged and a first flow channel 24 which is provided so as to face the first principal surface PS1 of the metal porous membrane 10. In Embodiment 1, the first recessed portion 23 is cylindrically recessed on the bottom of the first holding member 21 from the lower surface toward the upper surface of the first holding member 21. The first flow channel 24 is provided so as to extend from the first recessed portion 23 toward the upper surface of the first holding member 21.

The second holding member 22 is formed in a substantially cylindrical shape and has, on the inside thereof, a second recessed portion 25 in which the metal porous membrane 10 is arranged and a second flow channel 26 which is provided so as to face the second principal surface PS2 of the metal porous membrane 10. In Embodiment 1, the second recessed portion 25 is cylindrically recessed on the top of the second holding member 22 from the upper surface toward the lower surface of the second holding member 22. The second flow channel 26 is provided so as to extend from the second recessed portion 25 toward the lower surface of the second holding member 22.

The first holding member 21 and the second holding member 22 are engaged with each other with the metal porous membrane 10 interposed therebetween, and thus, the metal porous membrane 10 is held in a space S1 formed by the first recessed portion 23 and the second recessed portion 25.

As shown in FIG. 5A, the supply device 30 is mounted on the first holding member 21 of the holder 20. Specifically, the supply device 30 is detachably mounted on a first flow channel port 24a of the first flow channel 24 of the first holding member 21.

As shown in FIG. 5B, the backwash device 40 is mounted on the second holding member 22 of the holder 20. Specifically, the backwash device 40 is detachably mounted on a second flow channel port 26a of the second flow channel 26 of the second holding member 22.

The holder 20 may be, for example, formed of a gamma sterilizable or autoclave sterilizable material. The holder 20 may be, for example, formed of a material containing polyethylene, polyethylene terephthalate, polyurethane, polystyrene, silicone rubber, ABS resin, polyamide, polyamide-imide, polysulfone, polycarbonate, polyacetal, natural rubber, latex, urethane rubber, ethylene-vinyl acetate, polyester, epoxy, phenol, silica, alumina, gold, platinum, nickel, stainless steel, titanium, or the like.

<Supply Device>

The supply device 30 is a device which supplies a fluid 51 containing an object to be separated 50 to the metal porous membrane 10. The supply device 30 is, for example, a syringe or the like. Specifically, the supply device 30 includes an external cylinder which accommodates the fluid 51 and a plunger which is movable inside the external cylinder. As shown in FIG. 5A, the supply device 30 is mounted on the first flow channel port 24a of the first holding member 21 of the holder 20.

The supply device 30 supplies the fluid 51 containing the object to be separated 50 from the first principal surface PS1 of the metal porous membrane 10 toward the second principal surface PS2. For example, by pressing the fluid 51, the supply device 30 supplies the fluid 51 in the direction 60 from the first principal surface PS1 of the metal porous membrane 10 toward the second principal surface PS2. The fluid 51 from the supply device 30 is supplied through the first flow channel 24 of the first holding member 21 to the metal porous membrane 10. Thus, the object to be separated 50 that is larger than the through-hole 13 are made to be captured by the metal porous membrane 10.

Note that the supply device 30 may supply, by means of suction, the fluid 51 containing the object to be separated 50 in the direction 60 from the first principal surface PS1 of the metal porous membrane 10 toward the second principal surface PS2.

For example, the supply device 30 supplies the fluid 51 to the metal porous membrane 10 by being controlled by a control unit or the like.

<Backwash Device>

The backwash device 40 is a device which supplies a fluid 71 containing a plurality of particles 70 to the metal porous membrane 10 and backwashes the metal porous membrane 10 which has captured the object to be separated 50. The backwash device 40 is, for example, a syringe or the like. Specifically, the backwash device 40 includes an external cylinder which accommodates the fluid 71 and a plunger which is movable inside the external cylinder. As shown in FIG. 5B, the backwash device 40 is mounted on the second flow channel port 26a of the second holding member 22 of the holder 20.

The backwash device 40 supplies the fluid 71 containing the plurality of particles 70 from the second principal surface PS2 of the metal porous membrane 10 toward the first principal surface PS1. For example, by pressing the fluid 71, the backwash device 40 supplies the fluid 71 in the direction 61 from the second principal surface PS2 of the metal porous membrane 10 toward the first principal surface PS1. Thus, the fluid 71 from the backwash device 40 is supplied through the second flow channel 26 of the second holding member 22 to the metal porous membrane 10.

In Embodiment 1, preferably, the flow speed of the fluid 71 supplied from the backwash device 40 is higher than the flow speed of the fluid 51 supplied from the supply device 30.

For example, the backwash device 40 supplies the fluid 71 to the metal porous membrane 10 by being controlled by a control unit or the like.

Note that the backwash device 40 may supply, by means of suction, the fluid 71 containing a plurality of particles 70 in the direction 61 from the second principal surface PS2 of the metal porous membrane 10 toward the first principal surface PS1.

The particles 70 are formed of a material undergoing a small deformation due to external stress. Examples of the material constituting the particles 70 include silica, latex, metal, and the like.

The particles 70 are larger than a size of the through-hole 13 of the metal porous membrane 10. Here, the size of the through-hole 13 of the metal porous membrane 10 means the length of the shortest side among sides defining an opening of the through-hole 13. For example, the size of the through-hole 13 is the length of one side in the case where the opening of the through-hole 13 is in the shape of a square when viewed from the Z direction, and the length of the short side in the case of a rectangle. Furthermore, the size of the through-hole 13 is the diameter in the case where the opening of the through-hole 13 is in the shape of a circle when viewed from the Z direction, and the length of the minor axis in the case of an ellipse. In Embodiment 1, since the shape of the through-hole 13 is a square when viewed from the Z direction, the size the through-hole 13 means the length of one side D of the through-hole 13 shown in FIG. 4. For example, when the size of the through-hole is 1.8 µm, the particle size may be set to be 2 µm or 3 µm, and when the size of the through-hole is 2.5 µm, the particle size may be set to be 3 µm or 4 µm.

In Embodiment 1, the particles 70 are in the form of a circle. Therefore, the diameter of each of the particles 70 is larger than the size (the length of one side D) of the through-hole 13. Furthermore, preferably, the particle size of the particles 70 is smaller than a hole pitch P of the through-holes 13. The number of particles 70 contained in the fluid 71 is larger than the number of through-holes 13 of the metal porous membrane 10.

Furthermore, the plurality of particles 70 are formed with a uniform particle size. Note that, in the case where there is a large variation in particle size of the particles 70, classification may be performed using a filter in order to make the particle size of the particles 70 uniform. For example, the particles 70 may be subjected to classification using a metal porous membrane having a plurality of through-holes.

The fluid 71 is a fluid for backwashing. The fluid 71 may be any fluid as long as it does not damage the object to be separated 50. The fluid 71 may be the same as the fluid 51 supplied from the supply device 30. For example, in the case where the object to be separated 50 is a cell, the fluid 71 may be a cell culture solution or the like.

[Separation Recovery Method]

Figure 6:
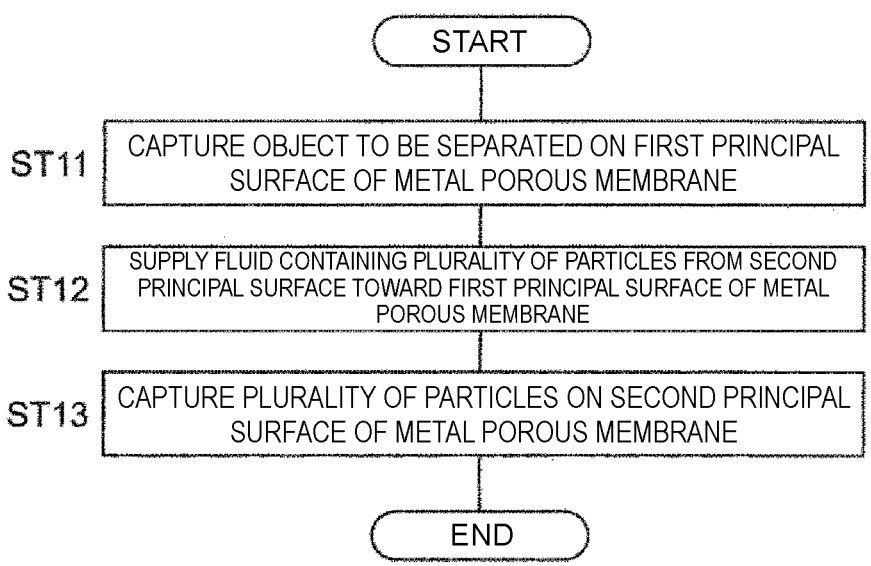
FIG. 6 is an example of a flowchart of a separation recovery method according to Embodiment 1 of the present invention.

A separation recovery method for an object to be separated according to Embodiment 1 of the present invention will be described with reference to FIG. 6. FIG. 6 is an example of a flowchart of a separation recovery method according to Embodiment 1 of the present invention.

As shown in FIG. 6, in step ST11, a fluid 51 containing an object to be separated is supplied from a first principal surface PS1 of a metal porous membrane 10 toward a second principal surface PS2. Thus, the fluid 51 is passed through the metal porous membrane 10, and the object to be separated 50 is captured on the first principal surface PS1 of the metal porous membrane 10.

Specifically, as shown in FIG. 5A, a supply device 30 is mounted on a first flow channel port 24a of a holder 20. The supply device 30 presses the fluid 51 containing a plurality of objects to be separated 50 in the direction 60 from the first principal surface PS1 of the metal porous membrane 10 toward the second principal surface PS2. Thus, the fluid 51 from the supply device 30 passes through a first flow channel 24 of a first holding member 21 of the holder 20 and is supplied to the metal porous membrane 10. In the metal porous membrane 10, while the fluid 51 passes through through-holes 13, the objects to be separated 50 larger than the through-hole 13 are captured on the first principal surface PS1 of the metal porous membrane 10.

After the objects to be separated 50 are captured on the first principal surface PS1 of the metal porous membrane 10, the supply device 30 is removed from the holder 20.

In step ST12, a fluid 71 containing a plurality of particles 70 larger than a size of the through-hole 13 of the metal porous membrane 10 is supplied to the metal porous membrane 10 which has captured the objects to be separated 50, from the second principal surface PS2 of the metal porous membrane 10 toward the first principal surface PS1. That is, in step ST12, the metal porous membrane 10 which has captured the objects to be separated 50 is backwashed by the fluid 71 containing a plurality of particles 70.

Specifically, as shown in FIG. 5B, a backwash device 40 is mounted on a second flow channel port 26a of the holder 20. The backwash device 40 presses the fluid 71 containing a plurality of particles 70 in the direction 61 from the second principal surface PS2 of the metal porous membrane 10 toward the first principal surface PS1. Thus, the fluid 71 from the backwash device 40 passes through the second flow channel 26 of the second holding member 22 of the holder 20 and is supplied to the metal porous membrane 10.

Although not shown in FIG. 5B, in Embodiment 1, a recovery device for recovering the objects to be separated 50 is mounted on the first flow channel port 24a of the holder 20. The recovery device recovers the objects to be separated 50 detached from the metal porous membrane 10 by backwashing with the backwash device 40. Examples of the recovery device include a container.

In step ST13, a plurality of particles 70 are captured on the second principal surface PS2 of the metal porous membrane 10. Specifically, by supplying the fluid 71 in step ST12, a plurality of particles 70 are captured in a plurality of through-holes 13 of the membrane portion 11 of the metal porous membrane 10.

Step ST13 will be described in detail with reference to FIGS. 7A to 7D. FIGS. 7A to 7D are each a schematic view showing an example of a step in the separation recovery method according to Embodiment 1 of the present invention. Note that FIGS. 7A to 7D are each an enlarged schematic view showing a part of the metal porous membrane 10.

Figure 7A:
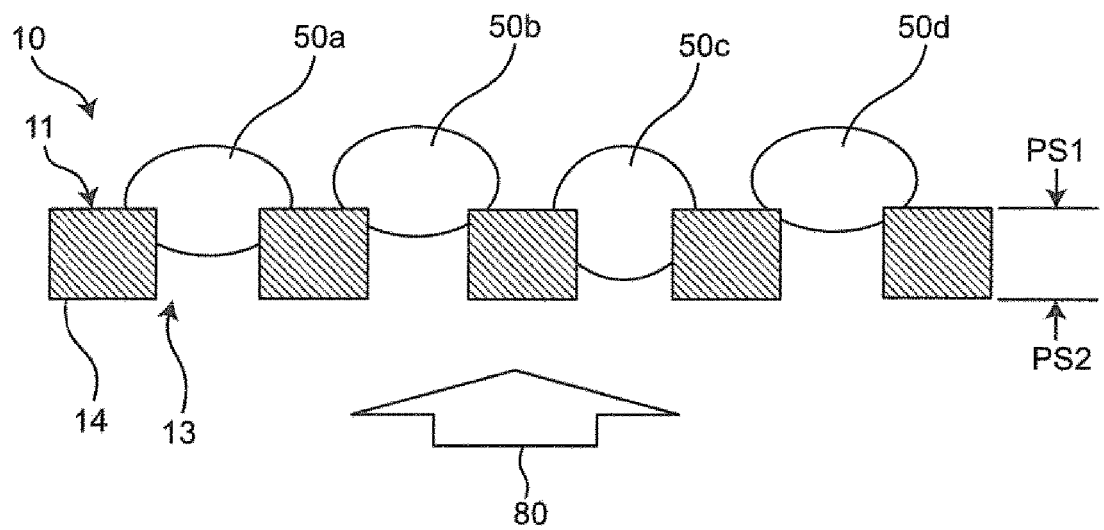
FIG. 7A is a schematic view showing a step of a separation recovery method according to Embodiment 1 of the present invention.

As shown in FIG. 7A, at the time of start of backwashing, objects to be separated 50a, 50b, 50c, and 50d are in the state of being captured on the first principal surface PS1 of the metal porous membrane 10. That is, at the time of start of backwashing, through-holes 13 are in the state of being blocked with the objects to be separated 50a, 50b, 50c, and 50d. Therefore, when the fluid 71 containing a plurality of particles 70 is supplied by the backwash device 40, a pressure 80 is generated, on the second principal surface PS2 side of the metal porous membrane 10, in the direction from the second principal surface PS2 toward the first principal surface PS1.

Here, the degrees of being stuck into the through-holes 13 of the objects to be separated 50a, 50b, 50c, and 50d are not uniform, but are different. FIG. 7A shows one example, in which the objects to be separated 50b and 50d are stuck shallowly into the through-holes 13 compared with the objects to be separated 50a and 50c.

Figure 7B:
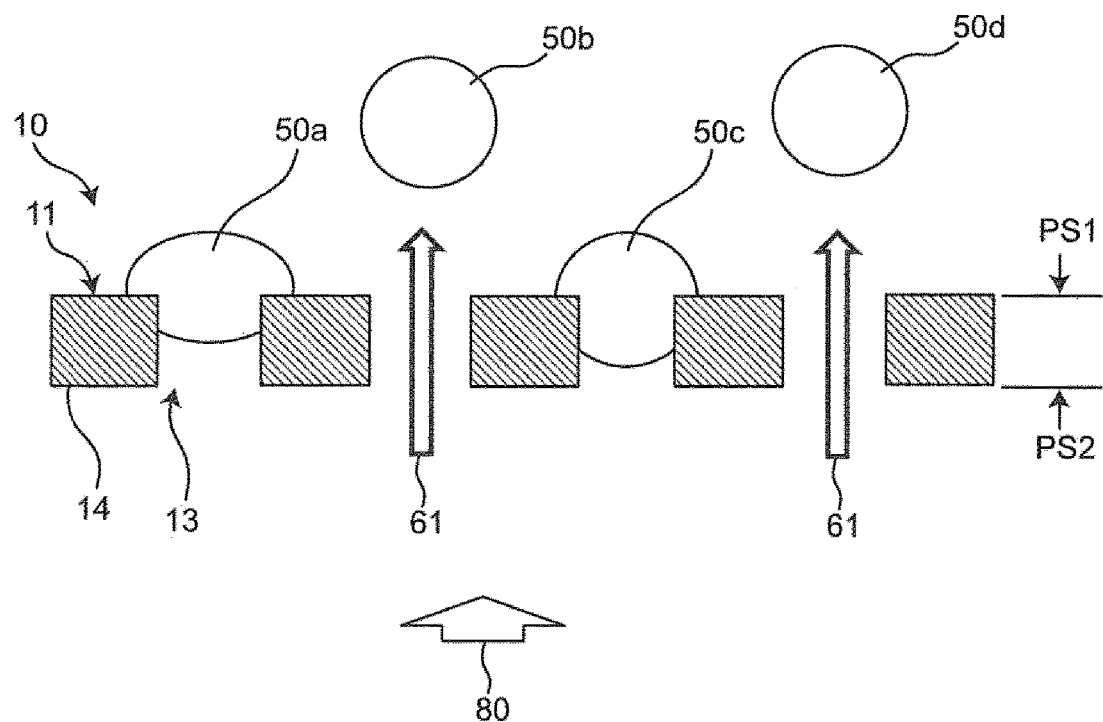
FIG. 7B is a schematic view showing a step of the separation recovery method according to Embodiment 1 of the present invention.

When the pressure 80 is applied to the second principal surface PS2 side of the metal porous membrane 10, as shown in FIG. 7B, the objects to be separated 50b and 50d which are stuck shallowly into the through-holes 13 are pushed out of the through-holes 13 and detached from the first principal surface PS1 of the metal porous membrane 10.

When the objects to be separated 50b and 50d are detached and removed from the through-holes 13, the fluid 71 for backwashing passes through the through-holes 13 from which the objects to be separated 50b and 50d have been removed and flows toward the first principal surface PS1 side of the metal porous membrane 10 (refer to arrows 61 shown in FIG. 7B). When the fluid 71 is allowed to pass through the through-holes 13, the pressure 80 applied to the second principal surface PS2 side of the metal porous membrane 10 is decreased, and the force for pushing the objects to be separated 50a and 50c remaining on the metal porous membrane 10 is decreased. Accordingly, as backwashing proceeds, it becomes difficult to detach the objects to be separated 50a and 50c from the through-holes 13.

Figure 7C:
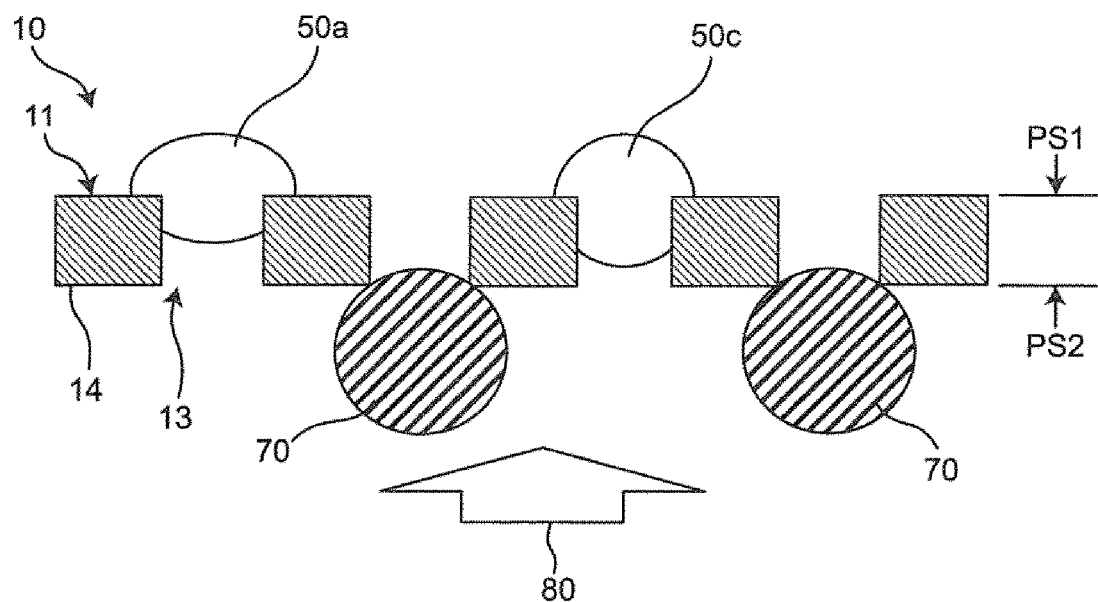
FIG. 7C is a schematic view showing a step of the separation recovery method according to Embodiment 1 of the present invention.

Next as shown in FIG. 7C, particles 70 are captured in the through-holes 13 from which the objects to be separated 50b and 50d have been removed on the second principal surface PS2 side of the metal porous membrane 10. That is, the through-holes 13 from which the objects to be separated 50b and 50d have been removed are blocked with the particles 70. Thus, the fluid 71 can be suppressed from passing through the through-holes 13, and the pressure 80 applied to the second principal surface PS2 side of the metal porous membrane 10 can be increased. Note that, in a square through-hole 13, as long as a spherical particle 70 is fitted into the through-hole 13, the four corners of the through-hole 13 may not be blocked with the particle 70.

Figure 7D:
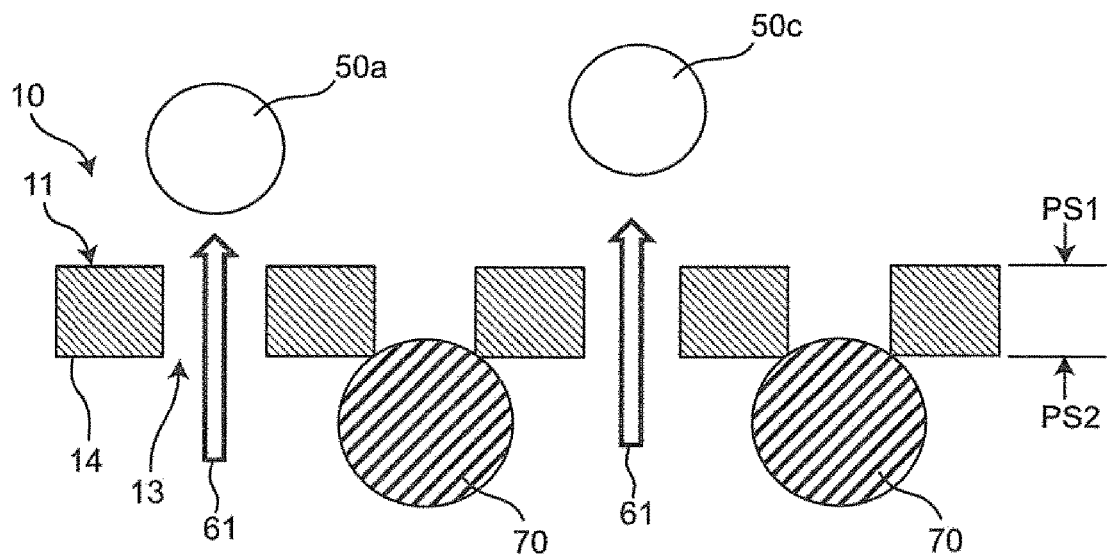
FIG. 7D is a schematic view showing a step of the separation recovery method according to Embodiment 1 of the present invention.

When the pressure 80 applied to the second principal surface PS2 side of the metal porous membrane 10 is increased, the force for pushing the objects to be separated 50a and 50c out of the through-holes 13 is increased. Thus, as shown in FIG. 7D, the objects to be separated 50a and 50c, which have been deeply stuck into the through-holes 13 compared with the objects to be separated 50*b* and 50*d*, can also be detached from the first principal surface PS1 of the metal porous membrane 10.

Advantageous Effects

In the separation recovery system 1 and the separation recovery method according to Embodiment 1, the following advantageous effects can be obtained.

In the separation recovery system 1 and the separation recovery method according to Embodiment 1, the object to be separated 50 is separated and recovered using the metal porous membrane 10. Consequently, in the separation recovery system 1 and the separation recovery method, the recovery ratio of the object to be separated 50 can be improved compared with the case where separation and recovery are performed using a membrane filter.

In the through-hole 13 of the metal porous membrane 10, the opening on the first principal surface PS1 side of the membrane portion 11 and the opening on the second principal surface PS2 side communicate with each other through a continuous wall surface. Furthermore, in the through-hole 13, the opening on the first principal surface PS1 side of the membrane portion 11 is provided so as to be projectable to the opening on the second principal surface PS2 side. In such a configuration, since a fluid can easily pass through the through-holes 13, the pressure drop during passing of the fluid can be decreased, compared with a membrane filter in which through-holes are formed in different directions three-dimensionally.

The metal porous membrane 10 can be designed so as to be thinner than a membrane filter. For example, the thickness of the metal porous membrane 10 can be designed to be smaller than the length of one side D of the through-hole 13. In such a configuration, since a fluid can easily pass compared with a membrane filter, the pressure drop can be decreased.

As described above, in the metal porous membrane 10, the pressure drop during passing of the fluid can be decreased, and therefore, in the case where the fluid 51 containing the object to be separated 50 is made to pass through the metal porous membrane 10 by pressing, the pressing force can be decreased. Consequently, since the object to be separated 50 can be suppressed from being deeply stuck into the through-holes 13, the object to be separated 50 can be easily detached from the metal porous membrane 10 during backwashing.

The object to be separated 50 is recovered by backwashing the metal porous membrane 10, using the fluid 71 containing a plurality of particles 70 larger than the size of the through-hole 13 of the metal porous membrane 10. By backwashing the metal porous membrane 10 with the fluid 71, the particles 70 are captured in the through-holes 13 out of which the object to be separated 50 has been pushed. In such a configuration, the through-holes 13 from which the object to be separated 50 has been removed can be blocked with the particles 70, and a decrease in the pressure 80 applied to the second principal surface PS2 side of the metal porous membrane 10 can be suppressed. Consequently, even in the state where backwashing advances, the object to be separated 50 stuck into the through-holes 13 can be pushed out of the through-holes 13, and therefore, the recovery ratio of the object to be separated 50 can be improved.

Preferably, the particles 70 are larger than the size (length of one side D of a square) of the through-hole 13 of the metal porous membrane 10 and smaller than the hole pitch P. In such a configuration, a plurality of particles 70 can block the through-holes 13 from the second principal surface PS2 side of the metal porous membrane 10, without obstructing one another, during backwashing. For example, the particles 70 captured in adjacent through-holes 13 can block the through-holes 13 with a distance therebetween. Thus, during backwashing, the through-holes 13 from which the object to be separated 50 has been removed can be efficiently blocked with the particles 70, and therefore, a decrease in the pressure 80 applied to the second principal surface PS2 side of the metal porous membrane 10 can be efficiently suppressed. Accordingly, the object to be separated 50 stuck into the through-holes 13 can be easily pushed out of the through-holes 13, and the recovery ratio of the object to be separated 50 can be improved.

The number of the particles 70 is greater than the number of the through-holes 13 of the metal porous membrane 10. In such a configuration, the through-holes 13 of the metal porous membrane 10 can be easily blocked with the particles 70. Thus, during backwashing, a decrease in the pressure 80 applied to the second principal surface PS2 side of the metal porous membrane 10 can be further suppressed, and the object to be separated 50 stuck into the through-holes 13 can be more easily pushed out of the through-holes 13.

The shape of each of the particles 70 is spherical. In such a configuration, the particles 70 roll on the second principal surface PS2 of the metal porous membrane 10 and become easily captured in the through-holes 13. Furthermore, in the case where the through-holes 13 are in the form of a square, even when a spherical particle 70 is captured in a through-hole 13, the through-hole 13 is not completely blocked, and gaps can be formed at the four corners. Since the gaps can let the fluid 71 flow out, it is possible to suppress the pressure 80 applied to the second principal surface PS2 side from increasing excessively to result in destruction of the metal porous membrane 10. Furthermore, by suppressing the pressure 80 from increasing excessively, it is also possible to suppress the object to be separated 50 from being destructed by the pressure 80.

Furthermore, spherical particles 70 can cope with various shapes of the through-holes 13 of the metal porous membrane 10. In the spherical particles 70, for example, even when each of the through-holes 13 has a shape other than a square, with a small variation in the state where the through-holes 13 are blocked, the spherical particles 70 can block the through-holes 13 evenly.

Embodiment 1 described an example in which the shape of each of the through-holes 13 is square. However, the present invention is not limited thereto. The shape of each of the through-holes 13 may be, for example, circular, elliptic, polygonal, rectangular, or the like.

Figure 8:
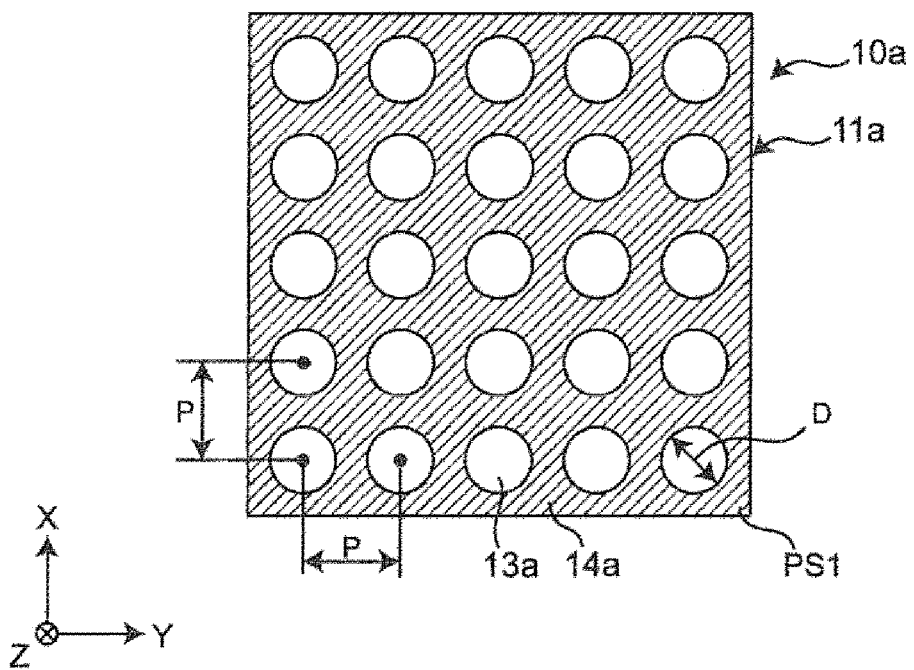
FIG. 8 is an enlarged cross-sectional view showing a part of a metal porous membrane according to a modification example in the separation recovery system according to Embodiment 1 of the present invention.

FIG. 8 is an enlarged cross-sectional view showing a part of a membrane portion 11*a* of a metal porous membrane 10*a* according to a modification example in the separation recovery system 1 according to Embodiment 1 of the present invention. As shown in FIG. 8, the membrane portion 11*a* may be formed of a filter base portion 14*a* provided with a plurality of circular through-holes 13*a*. Specifically, the through-holes 13*a* may have a circular shape when the metal porous membrane 10*a* is viewed from the first principal surface PS1 side, i.e., from the Z direction. The through-holes 13*a* are formed, for example, with a diameter D and a hole pitch P. Here, the hole pitch P of the circular through-holes 13*a* means the distance between a center of any through-hole 13*a* and a center of its adjacent through-hole 13*a*. In the case where the metal porous membrane 10*a* according to the modification example is used, particles 70 larger than the diameter D of the through-hole 13*a* and smaller than the hole pitch P are used.

In such a configuration, in the case where the particles 70 are spherical, the circular through-holes 13*a* are more likely to be blocked with the spherical particles 70 than the square through-holes 13. Furthermore, in the circular through-holes 13*a*, in the state of being blocked with particles 70, gaps can be made small compared with the square through-holes 13*a*. Therefore, by forming the through-holes 13 in the shape of a circle, a decrease in the pressure 80 applied to the second principal surface PS2 side of the metal porous membrane 10a can be further suppressed. As a result of this, the object to be separated 50 can be more easily pushed out of the through-holes 13a, and the recovery ratio of the object to be separated 50 can be further improved.

Embodiment 1 describes an example in which the particles 70 are spherical. However, the present invention is not limited thereto. The particles 70 may have a shape that can be captured in the through-holes 13. For example, the cross-sectional shape of each of the particles 70 may be different from the shape of the through-holes 13. In such a configuration, when the particles 70 are captured in the through-holes 13, by avoiding the through-holes 13 from being completely blocked with the particles 70, an escape route for the fluid 71 can be formed. As a result of this, during backwashing, it is possible to suppress the pressure 80 applied to the second principal surface PS2 side of the metal porous membrane 10 from increasing excessively to result in breakage of the metal porous membrane 10.

Embodiment 1 describes an example in which at the time of backwashing, by pressing the fluid 71 containing a plurality of particles 70, the backwash device 40 supplies the fluid 71 to the metal porous membrane 10. However, the present invention is not limited thereto. The backwash device 40 may supply the fluid 71 containing a plurality of particles 70 in the direction 61 from the second principal surface PS2 of the metal porous membrane 10 toward the first principal surface PS1 by setting a pressure on the second principal surface PS2 side of the metal porous membrane 10 higher than a pressure on the first principal surface PS1 side. For example, the fluid 71 containing a plurality of particles 70 may be supplied to the metal porous membrane 10 by suction or other method. In such a configuration, the recovery ratio of the object to be separated 50 can be improved.

Embodiment 1 describes an example in which, in the holder 20, the metal porous membrane 10 is sandwiched between the first holding member 21 and the second holding member 22. However, the present invention is not limited thereto. For example, the first holding member 21 and the second holding member 22 may be integrally formed.

Embodiment 1 describes an example in which the separation recovery system 1 includes the metal porous membrane 10, the holder 20, the supply device 30, and the backwash device 40. However, the present invention is not limited thereto. Constituent elements may be added or eliminated depending on the environment, circumstances, or the like in which the separation recovery system 1 is used. For example, the separation recovery system 1 may be a system which includes the metal porous membrane 10, the supply device 30, and the backwash device 40, without including the holder 20. Alternatively, in the case where only backwashing is performed on the metal porous membrane 10, without including the supply device 30, the system may be used as a backwashing system including the metal porous membrane 10, the holder 20, and the backwash device 40.

EXAMPLES (1) Example 1

In Example 1, using a separation recovery system 1 according to Embodiment 1, a separation and recovery experiment for an object to be separated 50 was performed.

In Example 1, HL-60 cells (Human promyelocytic leukemia cells) were used as the object to be separated 50, and a solvent (PBS (Phosphate Buffered Saline)) was used as the fluid 51. As the metal porous membrane 10, a metal mesh having a membrane portion 11 with a diameter of 6 mm and square-shaped through-holes 13 was used. The size (the length of one side D) of each of the through-holes 13 was 2.5 µm, and the hole pitch P of the through-holes 13 was 3.6 As the supply device 30 and the backwash device 40, a disposable syringe manufactured by Terumo Corporation and a syringe pump "YSP-201" manufactured by YMC Co., Ltd. were respectively used. As the particles 70, silica spherical particles with a particle size of 3 manufactured by Corefront Corporation were used. As the fluid 71, a solvent (PBS) was used.

The experiment will be specifically described below. In a $CO_2$ incubator, subculturing was performed for 7 days after seeding HL-60 cells. After incubation, the culture medium containing HL-60 cells was centrifuged at a centrifugal force of about 100 G to precipitate the HL-60 cells, then, the supernatant culture medium was removed, and the solvent was replaced with PBS. The number of cells in the HL-60 cell solution replaced with PBS was measured with a cell counter, and by adjusting the cell concentration in the solution using PBS, a standard solution with a cell concentration of $3\times10^6$ [number of cells/mL] was obtained.

By diluting the standard solution with PBS, four types of HL-60 cell solutions with cell concentrations of $3\times10^6$, $3\times10^5$, $3\times10^4$, and $3\times10^3$ [number of cells/mL] were prepared, and an ATP assay calibration curve was formed.

An ATP assay reagent "CA50" manufactured by Toyo Ink and each of the HL-60 cell solutions (0.5 mL each) were mixed in 24 wells, and the mixtures were left to stand under shading at room temperature for 10 minutes to allow reactions to proceed. Then, rocking was performed for one minute so as to obtain uniform solutions. Subsequently, using an ATP assay system "CL24-U" manufactured by Churitsu Electric Corporation, the light emission [cps] of each of the cell solutions after reaction with the reagent was measured, and a calibration curve in which the light emission Y [cps] and the number of cells X had the relationship $Y=1.94\times$ was obtained.

10 mL of a test solution obtained by diluting the standard solution with PBS to a cell concentration of $1.5\times10^4$ [number of cells/mL] (total number of cells in the solution: $1.5\times10^5$ cells) was placed into a disposable syringe manufactured by Terumo Corporation. Then, using a syringe pump "YSP-201" manufactured by YMC Co., Ltd., the test solution was passed through the metal porous membrane 10 at a flow speed of 0.006 [m/sec] (flow rate: 10 [mL/min]). In this way, the HL-60 cells in the solution were captured on the first principal surface PS1 of the metal porous membrane 10.

The metal porous membrane 10 by which separation of the HL-60 cells had been performed was removed from the holder 20, and the metal porous membrane 10 which had captured the HL-60 cells was immersed in a solution obtained by mixing the ATP assay reagent "CA50" and PBS (0.5 mL each) in 24 wells. Reagent reactions were carried out under the same conditions as those described above.

After reaction, the metal porous membrane 10 was taken out, and the light emission [cps] was measured using the ATP assay system. From the calibration curve, the number of HL-60 cells captured on the first principal surface PS1 of the metal porous membrane 10 was found to be $1.36\times10^5$ cells.

Next, after the metal porous membrane 10 which had captured the HL-60 cells was backwashed with the backwash device 40, the number of HL-60 cells remaining on the first principal surface PS1 of the metal porous membrane 10 was calculated. For comparison with Example 1, in Comparative Example 1, the number of HL-60 cells remaining on the first principal surface PS1 of the metal porous membrane 10 in the case where backwashing was performed using a fluid not containing the particles 70 was also calculated.

First, Example 1 will be described. In Example 1, using an aqueous solution of silica spherical particles with a particle size of 3 µm manufactured by Corefront Corporation, the solvent was replaced with PBS by centrifugation, and then an adjustment was made using PBS such that the particle concentration became $8 \times 10^4$ [number of particles/mL]. 10 mL of the silica particle solution whose concentration had been adjusted was placed into a disposable syringe manufactured by Terumo Corporation (number of silica particles in the solution: $8 \times 10^5$ particles), and the silica particle solution was passed through the metal porous membrane 10 at a flow speed of 0.006 [m/sec] (flow rate: 10 [mL/min]). In this way, backwashing was performed on the HL-60 cells captured on the first principal surface PS1 of the metal porous membrane 10.

The metal porous membrane 10 which had been backwashed was removed from the holder 20, and the metal porous membrane 10 which had been backwashed in Example 1 was immersed in a solution obtained by mixing the ATP assay reagent "CA50" and PBS (0.5 mL each) in 24 wells. Reagent reactions were carried out under the same conditions as those described above. After reaction, the metal porous membrane 10 was taken out, and the light emission [cps] was measured using the ATP assay system. From the calibration curve, the number of HL-60 cells remaining on the first principal surface PS1 of the metal porous membrane 10 after backwashing in Example 1 was obtained.

Next, Comparative Example 1 will be described. In Comparative Example 1, 10 mL of PBS serving as a fluid for backwashing was placed into a disposable syringe manufactured by Terumo Corporation, and using a syringe pump "YSP-201" manufactured by YMC Co., Ltd., PBS was passed through the metal porous membrane 10 at a flow speed of 0.006 [m/sec] (flow rate: 10 [mL/min]). In this way, backwashing was performed on the HL-60 cells captured on the first principal surface PS1 of the metal porous membrane 10.

The metal porous membrane 10 which had been backwashed was removed from the holder 20, and the metal porous membrane 10 which had been backwashed in Comparative Example 1 was immersed in a solution obtained by mixing the ATP assay reagent "CA50" and PBS (0.5 mL each) in 24 wells. Reagent reactions were carried out under the same conditions as those described above. After reaction, the metal porous membrane 10 was taken out, and the light emission [cps] was measured using the ATP assay system. From the calibration curve, the number of HL-60 cells remaining on the first principal surface PS1 of the metal porous membrane 10 after backwashing in Comparative Example 1 was obtained.

Experimental results in Example 1 and Comparative Example 1 are shown in Table 1.

TABLE 1

|  | Example 1 | Comparative Example 1 |
|---|---|---|
| Number of HL-60 cells captured on metal porous membrane before backwashing [number of cells] | $1.36 \times 10^5$ | |
| Number of HL-60 cells remaining on metal porous membrane after backwashing [number of cells] | $0.78 \times 10^4$ | $3.2 \times 10^4$ |
| Number of HL-60 cells recovered [number of cells] | $1.282 \times 10^5$ | $1.04 \times 10^5$ |
| Recovery ratio [%] | 94.3 | 76.4 |

As shown in Table 1, the number of HL-60 cells remaining on the metal porous membrane 10 after backwashing was $0.78 \times 10^4$ in Example 1 and $3.2 \times 10^4$ in Comparative Example 1. Based on the fact that the number of HL-60 cells captured on the metal porous membrane 10 before backwashing was $1.36 \times 10^5$, $1.282 \times 10^5$ HL-60 cells were recovered in Example 1 and $1.04 \times 10^5$ HL-60 cells were recovered in Comparative Example 1. The recovery ratio calculated was 94.3% in Example 1 and 76.4% in Comparative Example 1. Thus, it has been confirmed that the recovery ratio is improved in Example 1 compared with Comparative Example 1.

Furthermore, in Example 1 and Comparative Example 1, photographs of the metal porous membrane 10 before and after backwashing were taken with an SEM (Scanning Electron Microscope).

Figure 9A:
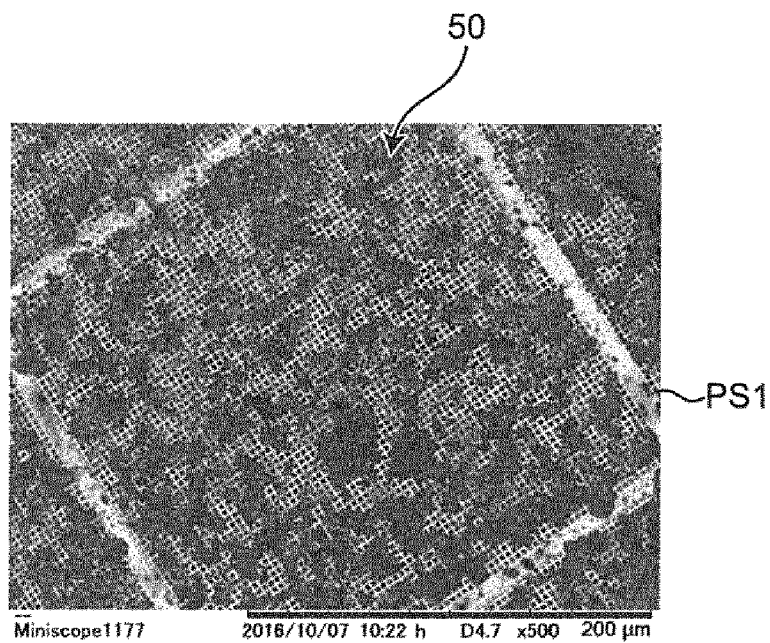
FIG. 9A is an enlarged photograph of a metal porous membrane before backwashing, taken from the first principal surface side.
Figure 9B:
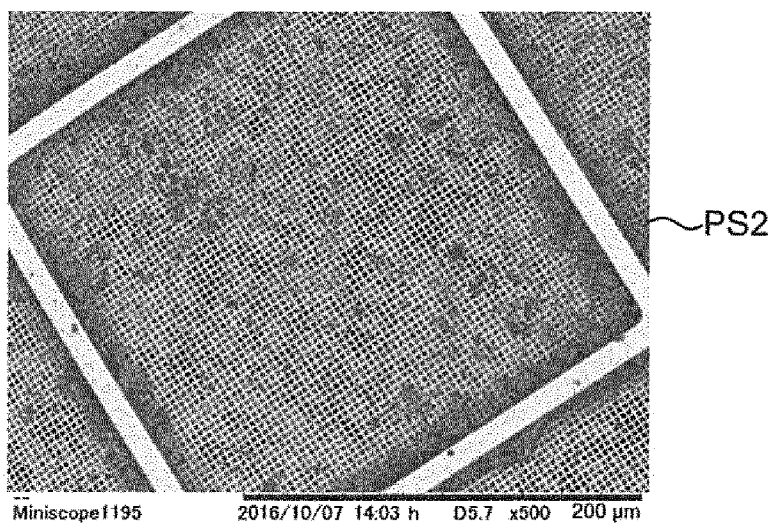
FIG. 9B is an enlarged photograph of a metal porous membrane before backwashing, taken from the second principal surface side.

FIG. 9A is an enlarged photograph of the metal porous membrane 10 before backwashing, taken from the first principal surface PS1 side. FIG. 9B is an enlarged photograph of the metal porous membrane 10 before backwashing, taken from the second principal surface PS2 side. As shown in FIG. 9A, HL-60 cells, i.e., the object to be separated 50, are captured on the first principal surface PS1 of the metal porous membrane 10. Furthermore, as shown in FIG. 9B, HL-60 cells stuck into the through-holes 13 can be observed from the second principal surface PS2 side of the metal porous membrane 10.

Figure 10A:
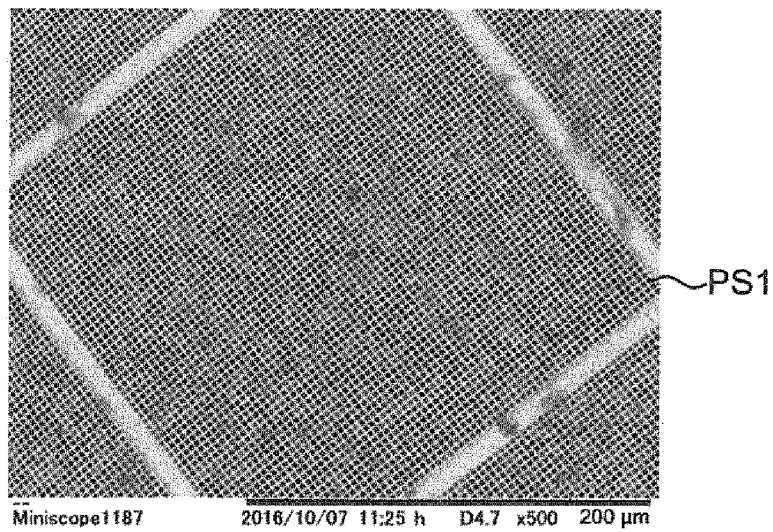
FIG. 10A is an enlarged photograph of a metal porous membrane after backwashing in Example 1, taken from the first principal surface side.
Figure 10B:
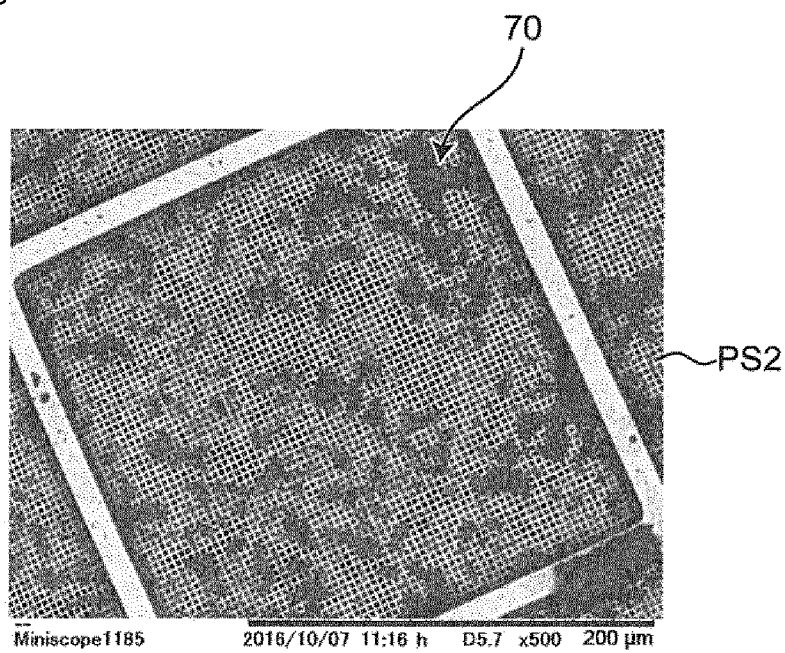
FIG. 10B is an enlarged photograph of the metal porous membrane after backwashing in Example 1, taken from the second principal surface side.

FIG. 10A is an enlarged photograph of the metal porous membrane 10 after backwashing in Example 1, taken from the first principal surface PS1 side. FIG. 10B is an enlarged photograph of the metal porous membrane 10 after backwashing in Example 1, taken from the second principal surface PS2 side. As shown in FIG. 10A, in Example 1, HL-60 cells hardly remain on the first principal surface PS1 after backwashing. Furthermore, as shown in FIG. 10B, in Example 1, silica particles, i.e. the particles 70, are captured on the second principal surface PS2 of the metal porous membrane 10 after backwashing. As is evident from the above, in Example 1, the HL-60 cells captured on the metal porous membrane 10 are detached from the first principal surface PS1 and recovered.

Figure 11A:
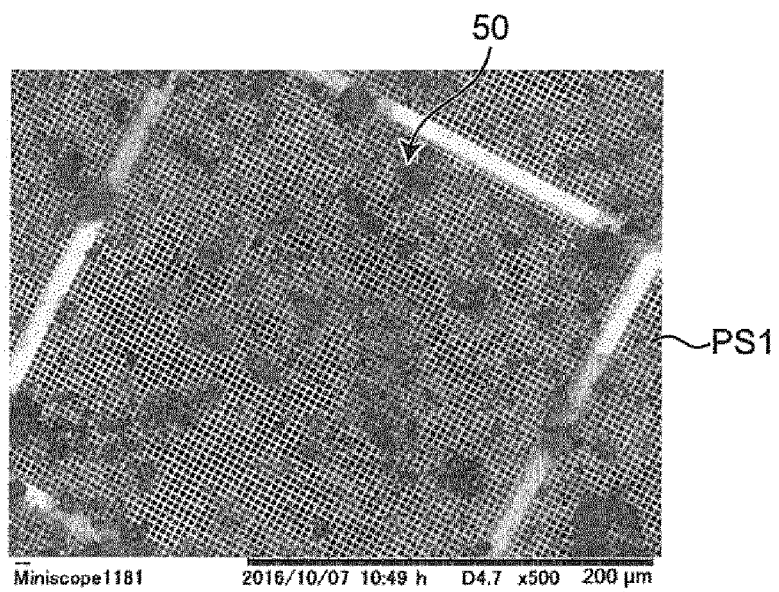
FIG. 11A is an enlarged photograph of a metal porous membrane after backwashing in Comparative Example 1, taken from the first principal surface side.
Figure 11B:
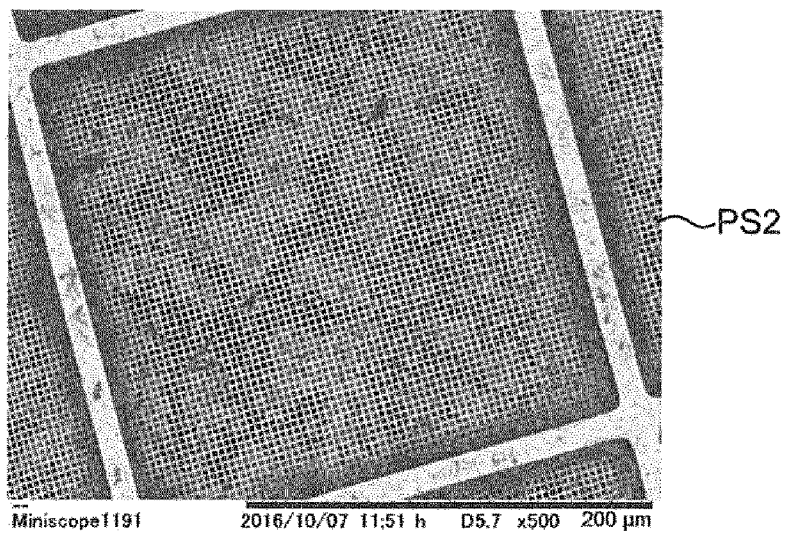
FIG. 11B is an enlarged photograph of the metal porous membrane after backwashing in Comparative Example 1, taken from the second principal surface side.

FIG. 11A is an enlarged photograph of the metal porous membrane 10 after backwashing in Comparative Example 1, taken from the first principal surface PS1 side. FIG. 11B is an enlarged photograph of the metal porous membrane 10 after backwashing in Comparative Example 1, taken from the second principal surface PS2 side. As shown in FIGS. 11A and 11B, in Comparative Example 1, some of the HL-60 cells remain in the metal porous membrane 10 after backwashing, and some of the HL-60 cells are unable to be recovered.

(2) Examples 2 to 4

In Examples 2 to 4, the same experiment as that of Example 1 was performed using as a parameter the concentration of particles 70.

In Examples 2 to 4, the experiment was performed using silica solutions with silica particle concentrations of $2.0 \times 10^5$ [number of particles/mL], $3.0 \times 10^5$ [number of particles/mL], and $4.0 \times 10^5$ [particles/mL], respectively. Experimental results in Examples 2 to 4 are shown in Table 2. Note that, in Table 2, the experimental results in Example 1 with a silica particle concentration of $8.0 \times 10^4$ [number of particles/mL] are also shown as reference.

TABLE 2

|  | Example 1 | Example 2 | Example 3 | Example 4 |
|---|---|---|---|---|
| Silica particle size [μm] | 3 | | | |
| Cross-sectional area of particle [mm$^2$] | $7.1 \times 10^6$ | | | |
| Number of particles [number] | $8.0 \times 10^5$ | $2.0 \times 10^6$ | $3.0 \times 10^6$ | $4.0 \times 10^6$ |
| Particle concentration [number of particles/mL] | $8.0 \times 10^4$ | $2.0 \times 10^5$ | $3.0 \times 10^5$ | $4.0 \times 10^5$ |
| Coverage [%] | 20 | 50 | 75 | 100 |
| Number of HL-60 cells captured on metal porous membrane before backwashing [number of cells] | $1.36 \times 10^5$ | | | |
| Number of HL-60 cells remaining on metal porous membrane after backwashing [number of cells] | $0.78 \times 10^4$ | $0.45 \times 10^4$ | $0.32 \times 10^4$ | $0.21 \times 10^4$ |
| Number of HL-60 cells recovered [number of cells] | $1.282 \times 10^5$ | $1.315 \times 10^5$ | $1.328 \times 10^5$ | $1.339 \times 10^5$ |
| Recovery ratio [%] | 94.3 | 96.7 | 97.6 | 98.5 |

In the present description, the term "coverage" means the number of silica particles in the particle solution for backwashing relative to the surface area (about 28.3 mm$^2$) of the membrane portion 11 of the metal porous membrane 10. Specifically, the coverage is defined by (coverage [%])= 100×(cross-sectional area of silica spherical particle [mm$^2$]×number of silica particles in particle solution [number])/(surface area of membrane portion 11 of metal porous membrane 10 [mm$^2$]).

As shown in Table 2, it has been confirmed that, in the order of Examples 1 to 4, as the silica particle concentration increases, the recovery ratio of HL-60 cells increases. That is, it is evident that as the coverage increases, the recovery ratio is improved.

Note that when the coverage exceeds 100%, the pressure applied to the metal porous membrane 10 during backwashing increases, and there is a possibility that the metal porous membrane 10 may be damaged.

From the results described above, it can be considered that the coverage is preferably 1% or more and 100% or less, and more preferably 10% or more and 100% or less.

(3) Examples 5 to 7

In Examples 5 to 7, the same experiment as that of Example 1 was performed using as a parameter the flow speed of the fluid 71 during backwashing. Specifically, in Examples 5 to 7, the experiment was performed at silica particle solution flow speeds of 0.003 [m/sec], 0.012 [m/sec], and 0.018 [m/sec], respectively. Experimental results in Examples 5 to 7 are shown in Table 3. Note that, in Table 3, the experimental results of the fluid 71 in Example 1 with a flow speed of 0.006 [m/sec] are also shown as reference.

TABLE 3

|  | Example 5 | Example 1 | Example 6 | Example 7 |
|---|---|---|---|---|
| Flow speed [m/sec] | 0.003 | 0.006 | 0.012 | 0.018 |
| Particle concentration [number of particles/mL] | $8.0 \times 10^4$ | | | |
| Number of HL-60 cells captured on metal porous membrane before backwashing [number of cells] | $1.36 \times 10^5$ | | | |
| Number of HL-60 cells remaining on metal porous membrane after backwashing [number of cells] | $1.2 \times 10^4$ | $0.78 \times 10^4$ | $0.48 \times 10^4$ | $0.19 \times 10^4$ |
| Number of HL-60 cells recovered [number of cells] | $1.24 \times 10^5$ | $1.282 \times 10^5$ | $1.312 \times 10^5$ | $1.341 \times 10^5$ |
| Recovery ratio [%] | 91.2 | 94.3 | 96.5 | 98.6 |

Figure 12:
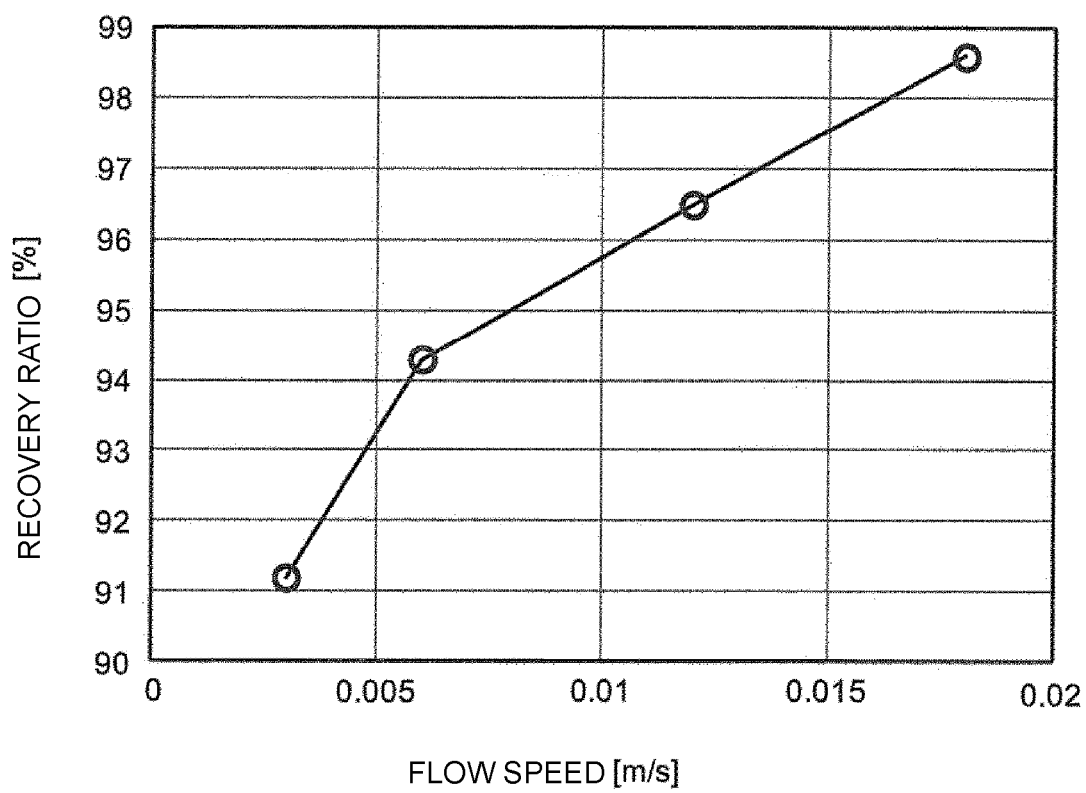
FIG. 12 is a graph showing the relationship between the flow speed of the fluid during backwashing and the recovery ratio in Example 1 and Examples 5 to 7.

FIG. 12 is a graph showing the relationship between the flow speed of the fluid during backwashing and the recovery ratio in Example 1 and Examples 5 to 7. As shown in Table 3 and FIG. 12, it has been confirmed that, in the order of Examples 5, 1, 6, and 7, as the flow speed of the silica particle solution during backwashing is increased, the recovery ratio increases. It is also evident that the slope of the graph changes greatly at the flow speed of the silica particle solution during backwashing of 0.006 m/sec as a boundary. This shows that the flow speed of the silica particle solution during backwashing is preferably 0.006 [m/sec] or more.

Although the present invention has been sufficiently described on the basis of the preferred embodiments with reference to the accompanying drawings, various alterations and modifications thereof are apparent to those skilled in the art. It is to be understood that such alterations and modifications are within the scope of the invention as long as they do not depart from the scope of the invention as defined by the appended claims.

The separation recovery system and the separation recovery method according to the present invention can be used in applications such as cell sorting, cell preparation, and cell screening, or applications such as in situ diagnosis/quick diagnosis of bacteria/viruses.

REFERENCE SIGNS LIST 1 separation recovery system
10, 10a metal porous membrane
11, 11a membrane portion
12 frame portion
13, 13a through-hole
14, 14a filter base portion
PS1 first principal surface
PS2 second principal surface
20 holder
21 first holding member
22 second holding member
23 first recessed portion
24 first flow channel
24a first flow channel port
25 second recessed portion
26 second flow channel
26a second flow channel port
30 supply device
40 backwash device
50, 50a, 50b, 50c, 50d object to be separated
51 fluid
60 direction
61 direction
70 particle
71 fluid
80 pressure

The invention claimed is:

1. A separation recovery method, the method comprising:
supplying a first fluid containing an object to be separated in a first direction from a first principal surface of a metal porous membrane having a plurality of through-holes toward a second principal surface facing the first principal surface so that the first fluid passes through the plurality of through-holes from a side of the first principal surface and the object to be separated is captured on the first principal surface of the metal porous membrane;
after the object to be separated is captured on the first principal surface of the metal porous membrane, supplying a second fluid containing a plurality of particles larger than a size of the plurality of through-holes of the metal porous membrane to the metal porous membrane on which the object to be separated has been captured in a second direction from the second principal surface of the metal porous membrane toward the first principal surface so that the second fluid passes through the plurality of through-holes from a side of the second principal surface; and
capturing the plurality of particles on the second principal surface of the metal porous membrane.

2. The separation recovery method according to claim 1, further comprising setting a pressure on the side of the second principal surface of the metal porous membrane higher than a pressure on the side of the first principal surface of the metal porous membrane when supplying the second fluid containing the plurality of particles in the second direction from the second principal surface of the metal porous membrane toward the first principal surface of the metal porous membrane.

3. The separation recovery method according to claim 1, wherein the plurality of particles are smaller than a hole pitch of the plurality of through-holes of the metal porous membrane.

4. The separation recovery method according to claim 1, wherein a number of the plurality of particles is greater than a number of the plurality of through-holes of the metal porous membrane.

5. The separation recovery method according to claim 1, wherein a shape of each of the plurality of particles is spherical.

6. The separation recovery method according to claim 1, wherein a shape of each of the plurality of through-holes of the metal porous membrane is circular when viewed from a thickness direction of the metal porous membrane.

7. The separation recovery method according to claim 1, wherein a shape of each of the plurality of through-holes of the metal porous membrane is square when viewed from a thickness direction of the metal porous membrane.

8. The separation recovery method according to claim 1, wherein a cross-sectional shape of each of the plurality of particles is different from a shape of the plurality of through-holes of the metal porous membrane.

9. The separation recovery method according to claim 1, wherein the first fluid is supplied by a syringe.

10. The separation recovery method according to claim 1, wherein the second fluid is supplied by a syringe.

* * * * *